(12) United States Patent
Tessien

(10) Patent No.: US 7,976,212 B2
(45) Date of Patent: Jul. 12, 2011

(54) APPARATUS FOR REPLENISHING A SOURCE GAS IN A CAVITATION MEDIUM

(75) Inventor: Ross Alan Tessien, Nevada City, CA (US)

(73) Assignee: Impulse Devices, Inc., Grass Valley, CA (US)

( * ) Notice: Subject to any disclaimer, the term of this patent is extended or adjusted under 35 U.S.C. 154(b) by 967 days.

(21) Appl. No.: 11/216,201

(22) Filed: Aug. 31, 2005

(65) Prior Publication Data

US 2007/0175526 A1    Aug. 2, 2007

Related U.S. Application Data

(63) Continuation-in-part of application No. 11/207,966, filed on Aug. 19, 2005.

(51) Int. Cl.
*B01F 11/00* (2006.01)
(52) U.S. Cl. ............ 366/114; 366/139; 366/148; 95/30; 95/249
(58) Field of Classification Search .................. 366/114, 366/115, 117, 118, 124, 127, 136, 137, 139, 366/144–149; 95/30, 241, 247–251, 260, 95/261
See application file for complete search history.

(56) References Cited

U.S. PATENT DOCUMENTS

| | | | |
|---|---|---|---|
| 1,492,764 A * | 5/1924 | Sumner et al. .................. | 303/10 |
| 2,450,885 A * | 10/1948 | Erdle .............................. | 264/299 |
| 2,643,816 A * | 6/1953 | Lewis .............................. | 417/63 |
| 3,357,912 A * | 12/1967 | Kiyoshi .................... | 204/224 M |
| 4,333,796 A | 6/1982 | Flynn | |

(Continued)

FOREIGN PATENT DOCUMENTS

WO    PCT/US95/15972    7/1996

(Continued)

OTHER PUBLICATIONS

Blake et al, Acoustic Cavitation:The Fluid Dynamics of Non-Spherical Bubbles, Phil. Trans. R. Soc. Lond. A, 1999, pp. 251-267, vol. 357, Publisher: The Royal Society, Published in: Great Britain.
M. Dan et al., Ambient Pressure Effect on Single-Bubble Sonoluminescence, Physical Review Letters, Aug. 30, 1999, pp. 1870-1873, vol. 83, No. 9, Publisher: The American Physical Society, Published in: US.

(Continued)

*Primary Examiner* — David L Sorkin
(74) *Attorney, Agent, or Firm* — C. Brandon Browning

(57) ABSTRACT

A cavitation system in which a source gas, e.g., a reactant, is loaded into the cavitation medium prior to cavitation is provided. The cavitation system includes a cavitation chamber with suitable cavitation drivers and a cavitation medium reservoir, the chamber and reservoir being flexibly coupled together via a pair of conduits. The conduits can be fabricated from a plastic or, as is preferred for higher temperature liquids, a metal. Typically metal conduits are formed into a coil, thus providing the desired flexibility. Flexibility is required in order to allow the relative positions of the cavitation chamber and the cavitation medium reservoir to be varied. The system is configured such that the cavitation fluid will flow out of the cavitation chamber, through the lower coupling conduit and into the cavitation medium reservoir when the chamber is positioned higher than the reservoir, and flow out of the cavitation medium reservoir, through the lower coupling conduit and into the cavitation chamber when the reservoir is positioned higher than the chamber. As a consequence of this configuration, cavitation fluid can be readily exchanged between the cavitation chamber and the cavitation medium reservoir, thereby aiding the degassing process as well as providing a means of replenishing reactant-depleted cavitation medium.

17 Claims, 9 Drawing Sheets

U.S. PATENT DOCUMENTS

| | | | |
|---|---|---|---|
| 4,563,341 | A | 1/1986 | Flynn |
| 5,659,173 | A | 8/1997 | Putterman et al. |
| 5,858,104 | A | 1/1999 | Clark |
| 5,968,323 | A | 10/1999 | Pless |
| 6,361,747 | B1 | 3/2002 | Dion et al. |
| 2002/0090047 | A1 | 7/2002 | Stringham |

FOREIGN PATENT DOCUMENTS

| | | |
|---|---|---|
| WO | WO 01/39200 A2 * | 5/2001 |
| WO | PCT/US02/16761 | 12/2002 |
| WO | PCT/CA03/00342 | 9/2003 |

OTHER PUBLICATIONS

Moss et al., Computed Optical Emissions from a Sonoluminescing Bubble, Physical Review E, Mar. 1999, pp. 2986-2992, vol. 59, No. 3, Published in: US.

Y.T. Didenko et al., Effect of Noble Gases on Sonoluminescence Temperatures during Multibubble Cavitation, Physical Review Letters, Jan. 24, 2000, pp. 777-780, vol. 84, No. 4, Publisher: The American Physical Society, Published in: US.

Gaitan et al, Experimental Observations of Bubble Response and Light Intensity Near the Threshold for Single Bubble Sonoluminscence, Physical Review E, May 1999, pp. 5495-5502, vol. 59, No. 5, Published in: US.

Barber et al, Sensitivity of Sonoluminescence to Experimental Parameters, Physical Review Letters, Feb. 28, 1994, pp. 1380-1382, vol. 72, No. 9, Published in: US.

F.R. Young, Sonoluminescence from Water Containing Dissolved Gases, J. Acoust. Soc. Am., Jul. 1996, pp. 100-104, vol. 60, No. 1, Publisher: Acoustical Society of America, Published in: US.

Putterman, Sonoluminescence:Sound Into Light, Scientific American, Feb. 1995, pp. 46-51.

Gaitan et al, Sonoluminescence and Bubble Dynamics for a Single, Stable, Cavitation Bubble, J. Acoust. Soc. Am., Jun. 1992, pp. 3166-3183, vol. 91, No. 6, Publisher: Acoustical Society of America, Published in: US.

Crum, Sonoluminescence, Physics Today, Sep. 1994, pp. 22-29, Publisher: American Institute of Physics, Published in: US.

Bollinger, Ultra Cavitation, http://wiretap.area.com/Gopher/Library/Article/Sci/cavitate.ult, Sep. 17, 2001, pp. 1-26.

* cited by examiner

APPARATUS FOR REPLENISHING A SOURCE GAS IN A CAVITATION MEDIUM

REFERENCE TO RELATED APPLICATIONS

This application is a continuation-in-part of U.S. patent application Ser. No. 11/207,966, filed Aug. 19, 2005.

FIELD OF THE INVENTION

The present invention relates generally to cavitation processes and, more particularly, to an apparatus for loading a source gas into a cavitation system.

BACKGROUND OF THE INVENTION

Sonoluminescence is a well-known phenomena discovered in the 1930's in which light is generated when a liquid is cavitated. Although a variety of techniques for cavitating the liquid are known (e.g., spark discharge, laser pulse, flowing the liquid through a Venturi tube), one of the most common techniques is through the application of high intensity sound waves.

In essence, the cavitation process consists of three stages; bubble formation, growth and subsequent collapse. The bubble or bubbles cavitated during this process absorb the applied energy, for example sound energy, and then release the energy in the form of light emission during an extremely brief period of time. The intensity of the generated light depends on a variety of factors including the physical properties of the liquid (e.g., density, surface tension, vapor pressure, chemical structure, temperature, hydrostatic pressure, etc.) and the applied energy (e.g., sound wave amplitude, sound wave frequency, etc.).

It is generally recognized that during the collapse of a cavitating bubble extremely high temperature plasmas are developed, leading to the observed sonoluminescence effect. This phenomena is at the heart of a considerable amount of research as scientists and engineers attempt to both completely characterize the phenomena and find applications for it. Noted applications include sonochemistry, chemical detoxification, ultrasonic cleaning and nuclear fusion.

U.S. Pat. No. 4,333,796 discloses a cavitation chamber comprised of a refractory metal such as tungsten, titanium, molybdenum, rhenium or some alloy thereof. Acoustic energy is supplied to the liquid (e.g., lithium or an alloy thereof) within the chamber by six metal acoustic horns coupled to transducers. The tips of the horns project into the chamber while the rearward portion of each horn is coupled to a heat exchanger system, the heat exchanger system withdrawing heat generated by the reactions within the chamber. The inventors note that by removing heat in this manner, the liquid remains within the chamber, thus avoiding the need to pump the chamber liquid. In one disclosed embodiment, the source (i.e., deuterium) is introduced into the cavitation medium through a conduit attached to the top of the chamber, the concentration of the source being controlled by the dissociation pressure over the surface of the host liquid. In an alternate disclosed embodiment, an external processing system with a combination pump and mixer removes deuterium and tritium gases released from the cavitation zone and trapped within the chamber or tritium gases trapped within the Li-blanket surrounding the chamber and then reintroduces the previously trapped deuterium and tritium into the cavitation zone via a conduit coupled to the cavitation chamber. Additional deuterium may also be introduced into the mixer.

U.S. Pat. No. 4,563,341, a continuation-in-part of U.S. Pat. No. 4,333,796, discloses a slightly modified, cylindrical cavitation chamber. The chamber is surrounded by an external heating coil which allows the liquid within the chamber to be maintained at the desired operating temperature. The system is degassed prior to operation by applying a vacuum through a duct running through the cover of the chamber. During operation, the inventor notes that graphite, dissolved in the host liquid metal, is converted to diamond. The diamond-rich host material is removed via an outlet duct adjacent to the bottom of the chamber and graphite-rich host material is removed via an outlet duct adjacent to the upper end of the chamber. Additional host material and graphite are added by lowering rods comprised of the host material and graphite, respectively, into the heated chamber.

U.S. Pat. No. 5,659,173 discloses a sonoluminescence system that uses a transparent spherical flask fabricated from Pyrex®, Kontes®, quartz or other suitable glass and ranging in size from 10 milliliters to 5 liters. The inventors disclose that preferably the liquid within the flask is degassed and the flask is sealed prior to operation. In one disclosed embodiment, the cavitation chamber is surrounded by a temperature control system, thus allowing the liquid within the chamber to be cooled to a temperature of 1° C. Bubbles are introduced into the cavitation fluid using a variety of techniques including dragging bubbles into the fluid, for example with a probe, and localized boiling.

U.S. Pat. No. 5,858,104 discloses a shock wave chamber partially filled with a liquid. The remaining portion of the chamber is filled with gas which can be pressurized by a connected pressure source. Acoustic transducers mounted in the sidewalls of the chamber are used to position an object within the chamber while another transducer delivers a compressional acoustic shock wave into the liquid. A flexible membrane separating the liquid from the gas reflects the compressional shock wave as a dilatation wave focused on the location of the object about which a bubble is formed.

U.S. Pat. No. 5,968,323 discloses a cavitation chamber filled with a low compressibility liquid such as a liquid metal, the chamber enclosed within a temperature controlled container. A sealed fluid reservoir is also enclosed within the temperature controlled container, the reservoir connected to the bottom of the cavitation chamber by a pipe. By pressurizing or evacuating the reservoir, fluid can be forced into or withdrawn from the cavitation chamber. Fluid flow into or out of the chamber is aided by a vacuum pump and a pressurized gas source coupled to the top of the cavitation chamber. The system includes two material delivery systems for introducing materials or mixtures of materials into the chamber. One of the delivery systems is coupled to the bottom of the chamber and is intended for use with materials of a lower density than that of the cavitation liquid, thus causing the material to float upwards. The second delivery system is coupled to the top of the chamber and is intended for use with materials of a higher density than that of the cavitation liquid, thus causing the material to sink once introduced into the chamber.

PCT Application No. US02/16761 discloses a nuclear fusion reactor in which at least a portion of the liquid within the reactor is placed into a state of tension, this state of tension being less than the cavitation threshold of the liquid. The liquid preferably includes enriched deuterium or tritium, the inventors citing deuterated acetone as an exemplary liquid. In at least one disclosed embodiment, acoustic waves are used to pretension the liquid. After the desired state of tension is obtained, a cavitation initiation source, such as a neutron source, nucleates at least one bubble within the liquid, the bubble having a radius greater than a critical bubble radius.

The nucleated bubbles are then imploded, the temperature generated by the implosion being sufficient to induce a nuclear fusion reaction.

PCT Application No. CA03/00342 discloses a nuclear fusion reactor in which a bubble of fusionable material is compressed using an acoustic pulse, the compression of the bubble providing the necessary energy to induce nuclear fusion. The nuclear fusion reactor is spherically shaped and filled with a liquid such as molten lithium or molten sodium. A pressure control system is used to maintain the liquid at the desired operating pressure. To form the desired acoustic pulse, a pneumatic-mechanical system is used in which a plurality of pistons associated with a plurality of air guns strike the outer surface of the reactor with sufficient force to form a shock wave within the liquid in the reactor. In one disclosed embodiment, the spherical reactor is coupled to a fluid flow circuit in which a pump and a valve control the flow of fluid. A reservoir containing a fusionable material, preferably in gaseous form, is in communication with the fluid flow circuit. When desired, a bubble of the fusionable material, preferably encapsulated in a spherical capsule, is released from the reservoir and into the fluid flow circuit, which then injects the bubble into a port at the bottom of the chamber.

Co-pending U.S. patent application Ser. No. 11/001,720, filed Dec. 1, 2004, discloses a system for circulating cavitation fluid within a closed-loop fluid circulatory system coupled to the cavitation chamber. Cavitation fluid can be circulated throughout the system before, during or after cavitation chamber operation. As disclosed, a network of conduits couples the cavitation chamber to a cavitation fluid reservoir and at least one external fluid pump. Manipulation of various valves within the conduit network allows the cavitation fluid to either be pumped from the reservoir into the cavitation chamber or from the cavitation chamber into the reservoir. The disclosed system provides a means of draining and/or filling the cavitation chamber with minimal, if any, exposure of the cavitation fluid to the outside environment.

Although a variety of sonoluminescence systems have been designed, they do not provide an efficient system for introducing or replacing a source, e.g., a reactant, into the cavitation medium. Accordingly, what is needed is a cavitation fluid circulatory system that can be used for source replenishment, preferably without re-pressurizing the entire cavitation system. The present invention provides such a system.

SUMMARY OF THE INVENTION

The present invention provides a cavitation system in which a source gas, e.g., a reactant, is loaded into the cavitation medium prior to cavitation. The system allows the cavitation medium which has been at least partially depleted of reactant to be replaced with non-depleted cavitation medium, reactant depletion resulting from the cavitation process.

The cavitation system of the invention includes a cavitation chamber with suitable cavitation drivers and a cavitation medium reservoir, the chamber and reservoir being flexibly coupled together via a pair of conduits. The conduits can be fabricated from a plastic or, as is preferred for higher temperature liquids, a metal. Typically metal conduits are formed into a coil, thus providing the desired flexibility. Flexibility is required in order to allow the relative positions of the cavitation chamber and the cavitation medium reservoir to be varied. The system is configured such that the cavitation fluid will flow out of the cavitation chamber, through the lower coupling conduit and into the cavitation medium reservoir when the chamber is positioned higher than the reservoir, and flow out of the cavitation medium reservoir, through the lower coupling conduit and into the cavitation chamber when the reservoir is positioned higher than the chamber. As a consequence of this configuration, cavitation fluid can be readily exchanged between the cavitation chamber and the cavitation medium reservoir, thereby aiding the degassing process as well as providing a means of replenishing reactant-depleted cavitation medium.

In another aspect of the invention, a vacuum system is coupled to the cavitation system for use during degassing procedures. The vacuum system may include a cold trap. A pressurized gas source is also coupled to the cavitation system, the gas source used to load the cavitation medium with the desired reactant. Preferably multiple valves are used to couple/de-couple the vacuum system and the gas source to the cavitation system when required, for example as a means of protecting pressure gauges attached to the vacuum system.

In one embodiment of the invention, the cavitation medium has a melting temperature higher than the ambient temperature (e.g., metal, salt). In order to accommodate such a medium, the cavitation chamber, cavitation medium reservoir, and any coupling conduits in which the cavitation fluid is expected to flow are heated to a temperature greater than the melting temperature of the cavitation medium. Preferably in this embodiment the system components that must be heated are located within an oven. Alternately the desired temperature can be reached using localized heaters to heat the chamber, reservoir and those portions of the conduits through which the cavitation fluid must pass.

A further understanding of the nature and advantages of the present invention may be realized by reference to the remaining portions of the specification and the drawings.

DESCRIPTION OF THE SPECIFIC EMBODIMENTS

Figure 1:
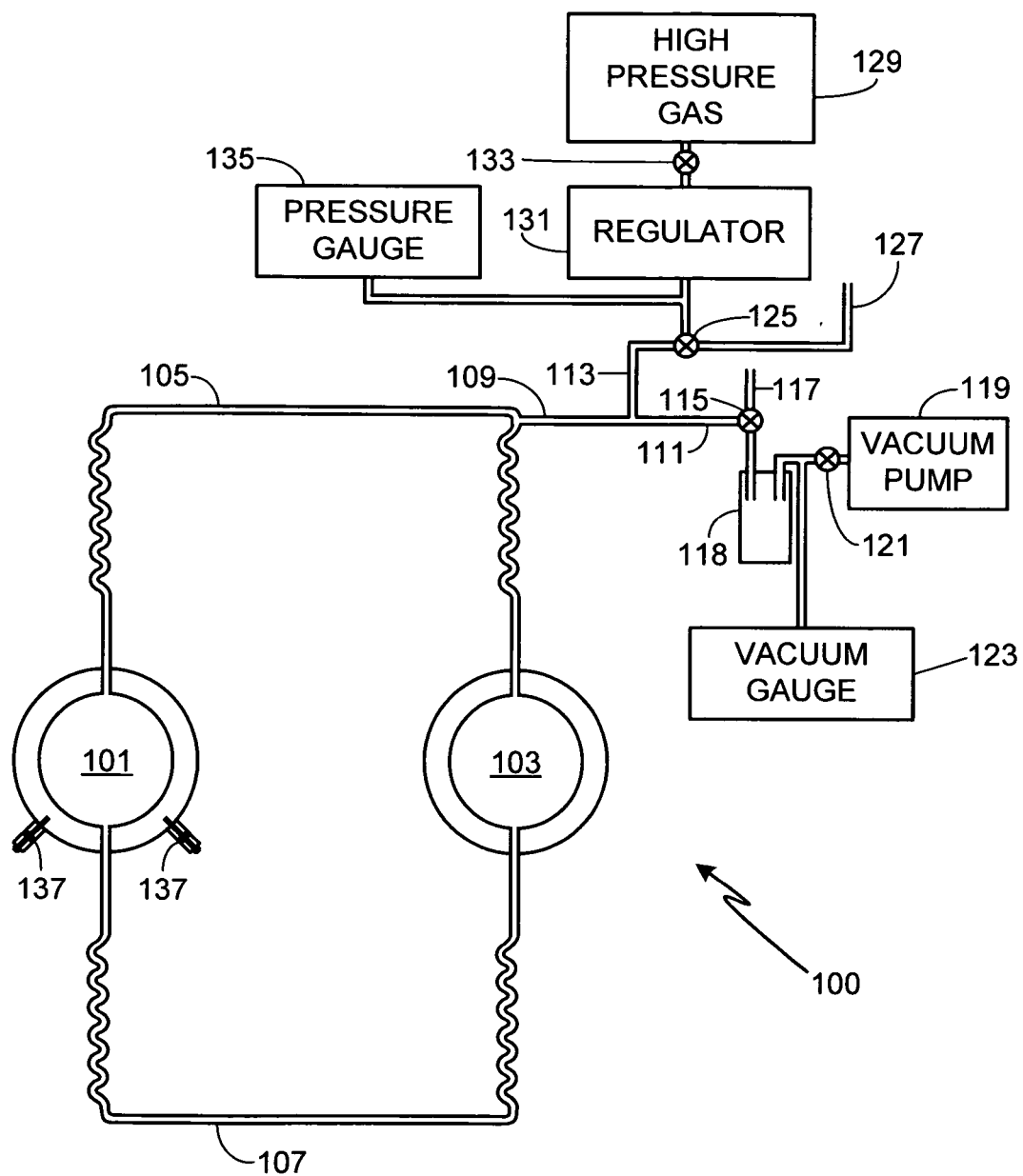
FIG. 1 is an illustration of the primary components of a system configured in accordance with the invention.

FIG. 1 is an illustration of one embodiment of the invention. System 100 includes a cavitation chamber 101 in which the desired cavitation processes, for example cavitation driven reactions, are performed. System 100 also includes a cavitation fluid reservoir 103. Coupling chamber 101 to reservoir 103 is an upper conduit 105 and a lower conduit 107, conduits 105 and 107 having sufficient flexibility to allow the relative vertical positions of chamber 101 and reservoir 103 to be varied as described below while still remaining coupled together.

In illustrated system 100 as well as at least one preferred embodiment of the invention, cavitation chamber 101 is a spherical chamber. It will be appreciated, however, that the invention is not limited to spherical chambers, rather chamber 101 can utilize any chamber design which is suitable for the intended cavitation process. Examples of other configurations include cylindrical chambers, hourglass-shaped chambers, conical chambers, cubical chambers, rectangular chambers, irregularly-shaped chambers, etc. One method of fabricating chamber 101 is described in detail in co-pending U.S. patent application Ser. No. 10/925,070, filed Aug. 23, 2004, entitled Method of Fabricating a Spherical Cavitation Chamber, the entire disclosure of which is incorporated herein for any and all purposes. Examples of hourglass-shaped chambers are provided in co-pending U.S. patent application Ser. No. 11/140,175, filed May 27, 2005, entitled Hourglass-Shaped Cavitation Chamber, and Ser. No. 11/149,791, filed Jun. 9, 2005, entitled Hourglass-Shaped Cavitation Chamber with Spherical Lobes, the entire disclosures of which are incorporated herein for any and all purposes. An example of a cylindrical cavitation chamber is provided in co-pending U.S. patent application Ser. No. 11/038,344, filed Jan. 18, 2005, entitled Fluid Rotation System for a Cavitation Chamber, the entire disclosure of which is incorporated herein for any and all purposes.

Chamber 101 can be fabricated from any of a variety of materials, depending primarily upon the desired operating pressure and temperature of the chamber and system. Preferably the selected material is machinable, thus simplifying fabrication, and corrosion resistant, thus allowing the chamber to be used repeatedly with a variety of liquids. Typically a metal, for example 17-4 precipitation hardened stainless steel, is used for chamber 101.

The selected dimensions of chamber 101 depend primarily on the intended use of the chamber, although the cost of the cavitation fluid, chamber fabrication issues, operating temperature and cavitation driver capabilities also influence the preferred dimensions of the chamber for a specific process. In general, small chambers are preferred for situations in which it is desirable to limit the amount of the cavitation medium or in which driver input energy is limited while large chambers (e.g., 10 inches or greater) are preferred as a means of simplifying experimental set-up and event observation or when high energy reactions are being driven within the chamber. Thick chamber walls are preferred in order to accommodate high pressures.

In a preferred embodiment of the invention, as illustrated in FIG. 1, the internal volumes of chamber 101 and reservoir 103 are approximately equal. It should be appreciated, however, that the chambers do not have to be of the same internal volume. For example, the reservoir can be designed to hold more cavitation fluid than cavitation chamber 101. Additionally, reservoir 103 does not have to be shaped the same as chamber 101. In general, reservoir 103 is designed to simply handle the desired operating pressure and temperature while being relatively simple to manufacture, assemble, and couple to system 100. Thus while chamber 101 may be designed to meet certain criteria associated with the intended cavitation process, for example to enhance the performance of the selected driver with a specific cavitation fluid, the design limitations placed on reservoir 103 are much less taxing. As a result, chamber 101 and reservoir 103 may utilize the same design (e.g., both spheres), or completely different designs (e.g., an hourglass-shaped cavitation chamber and a spherical reservoir).

Conduits 105 and 107 are required to provide the necessary positional flexibility of chamber 101 relative to reservoir 107 while handling the desired operating pressure and temperature of the cavitation fluid. Thus, for example, a plastic (e.g., polyvinyl chloride, chlorinated polyvinyl chloride, polyethylene, cross-linked polyethylene or PEX, etc.) can be used for low temperature applications while a metal (e.g., coiled copper tubing, coiled stainless steel tubing, etc.) is preferably used for higher temperature applications. Any of a variety of non-metallic cavitation media can be used, for example acetone. The primary limitation placed on a metal cavitation medium is the temperature capabilities of system 100. To simplify the design and fabrication of system 100, preferably a metal with a relatively low temperature melting point is used such as mercury or a cerro metal (e.g., cerrobend). Higher melting point metals or salts can be used in system 100 if the system is capable of operating at or above the melting point of the desired metal or salt.

A third conduit 109 is attached to either upper conduit 105, for example as shown, or attached to the upper portion of reservoir 103 (not shown). Conduit 109 allows the system to be coupled to a vacuum system for evacuation and coupled to a pressurized gas system for supplying the desired gas for loading the cavitation medium. Although not preferred, it should be understood that the gas loading system and the degassing system (i.e., vacuum pump) can be attached to system 100 (e.g., conduit 105) in separate locations. Conduit 109 can also be used to fill the system with the cavitation medium. Alternately a separate cavitation medium filling system can be used as described in further detail below.

In the preferred embodiment, conduit 109 tees or splits into two branches, conduit 111 leading to the vacuum system and conduit 113 leading to the gas loading system. A three-way valve 115 allows the system to be coupled to the ambient atmosphere via conduit 117 or to vacuum pump 119. Valve 121 provides a means for isolating the system from pump 119. Preferably a trap 118 insures that cavitation fluid is not drawn into vacuum pump 119 or vacuum gauge 123. Preferably trap 118 is cooled so that any cavitation medium entering the trap solidifies. Typically at least one vacuum gauge 123 is used to provide an accurate assessment of the system pressure. Three-way valve 125 allows the system to be coupled to the ambient atmosphere via conduit 127 or to the high pressure gas source 129. A pressure regulator 131 is used to control the output pressure of source 129. Valve 133 controls the output of source 129. Typically at least one pressure gauge 135 is used to monitor the system pressure.

Figure 2:
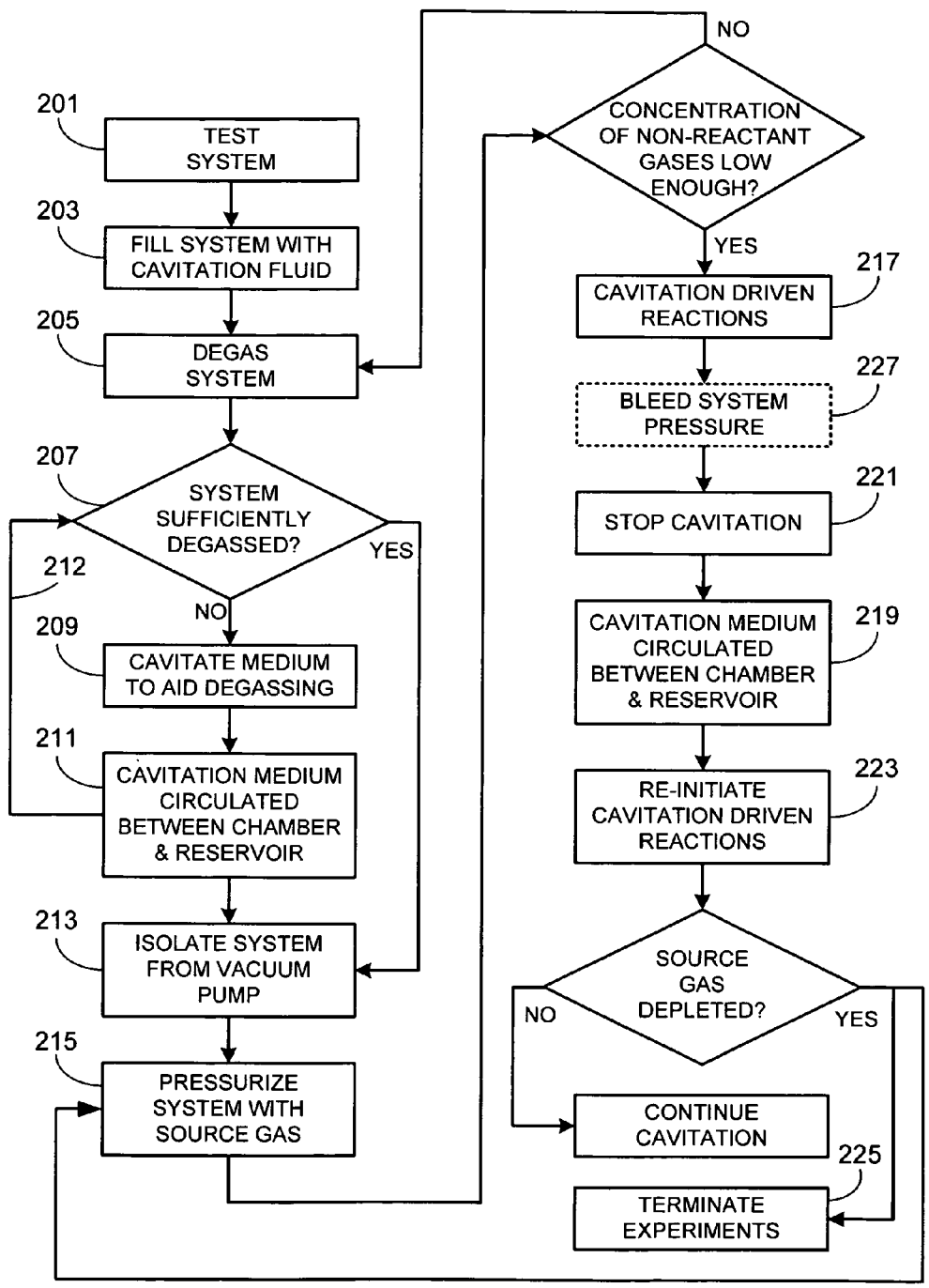
FIG. 2 illustrates the steps performed during use of the gas loading system shown in FIG. 1.

FIG. 2 illustrates the primary steps performed during the use of the gas loading system of the invention. Initially the system is tested for leaks using a two step process (step 201). First, the entire system is evacuated using vacuum pump 119 in order to verify that the system does not have any leaks while under vacuum. Second, the entire system is pressurized, for example using a high pressure nitrogen or helium source. The high pressure gas source which is used during testing can be attached where source gas 129 is typically attached, or separately coupled to system 100. Typically system 100 is tested at least at the highest expected pressure (e.g., operating pressure, gas loading pressure), on the order of 500 to 1000 psi in the preferred embodiment, and at the desired operating temperature.

If the system does not exhibit any leaks while evacuated or pressurized, or after any leaks have been fixed, it is then filled with the cavitation medium (step 203). The system is filled with sufficient cavitation medium to fill cavitation chamber 101 to the desired operating level, partially fill reservoir 103 and completely fill conduit 107 coupling the lower portions of chamber 101 and reservoir 103. It will be appreciated that the operating level for chamber 101 is based on obtaining the most efficient cavitation action. For example, while a spherical chamber (e.g., the chamber shown in FIG. 1) may be most efficiently operated when it is completely full, a vertically aligned cylindrical chamber may operate most efficiently when it is not completely full, thus providing a free cavitation liquid surface at the top of the chamber. With respect to reservoir 103, the level to which it is filled depends upon its size. For example, assuming that reservoir 103 is of approximately the same inner volume as chamber 101, it is filled to about 25 percent capacity. The exact level to which reservoir 103 is filled is not critical. The purpose is to insure that reservoir 103 has sufficient unfilled volume to allow a large portion, if not all, of the medium contained within chamber 101 to be transferred into reservoir 103 during the medium mixing step discussed below. Furthermore it is desirable for the medium within reservoir 103 to have a relatively large surface area, thus improving the efficiency of both the degassing and the gas loading steps discussed below. It will be appreciated that if during the cavitation medium filling step the relative positions of chamber 101 and reservoir 103 are approximately equal as illustrated in FIG. 1, and assuming approximately equivalent internal volumes, the chamber and reservoir would each be approximately ⅝'s filled in order to achieve the desired fill volumes noted above.

Figure 3:
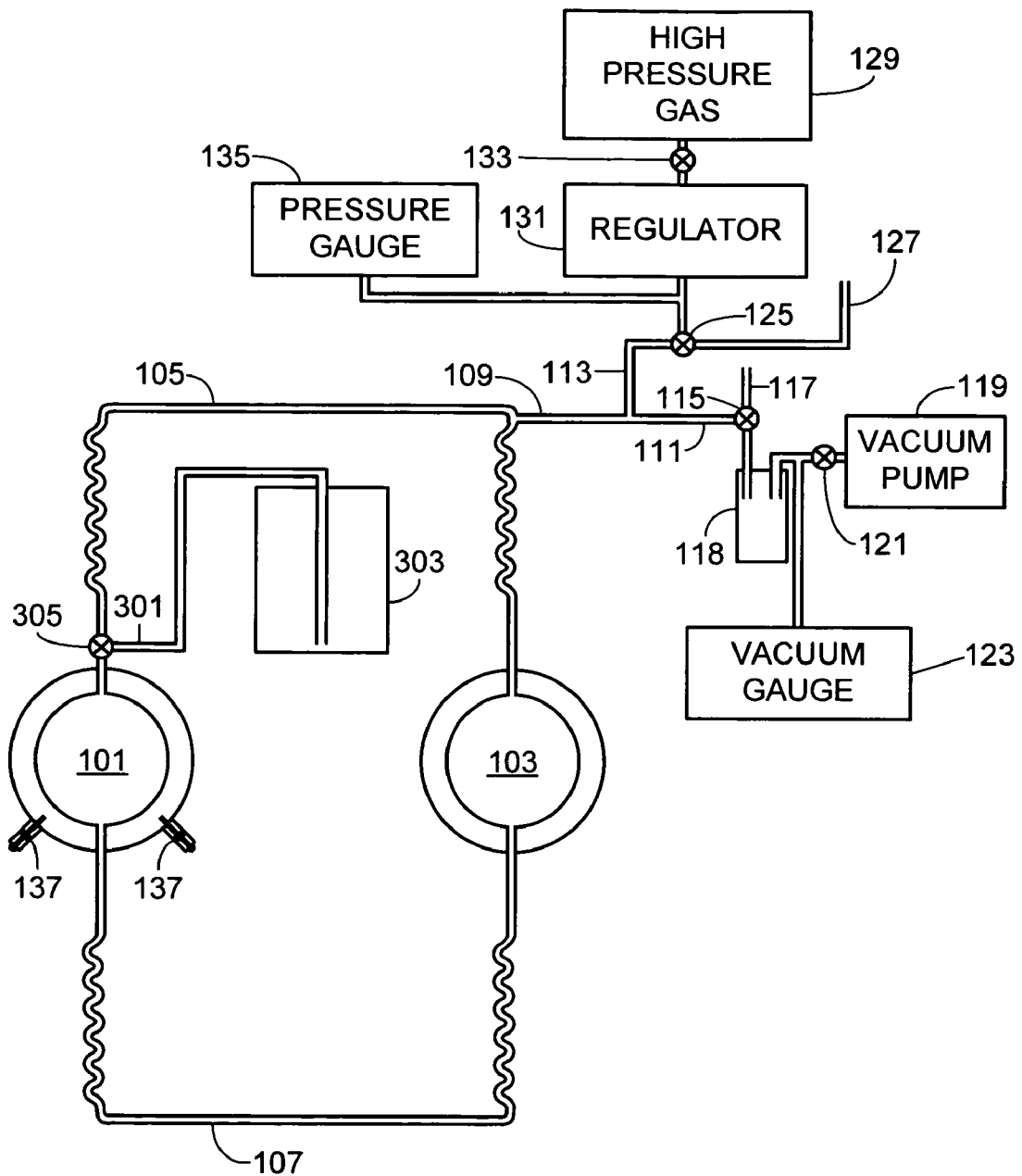
FIG. 3 is an illustration of a system similar to that shown in FIG. 1, showing an alternate means of coupling the system to the cavitation medium filling reservoir.

System 100 can be filled, for example, via either conduit 117 or 127. Alternately, as illustrated in FIG. 3, a different conduit 301 can be used for system filling. Regardless of the fill conduit, preferably a reservoir 303 is coupled to the selected conduit (note: reservoir 303 is only shown coupled to conduit 301 although a similar reservoir can be used with conduit 117 or conduit 127). In the system illustrated in FIG. 3, conduit 301 is coupled to conduit 105 via a three-way valve 305. Alternately, conduit 105 can be disconnected from chamber 101 and conduit 301 connected to chamber 101 for filling, and then, once the system is filled to the desired level, reversed (i.e., re-coupling conduit 105 to chamber 101). Regardless of the method used to couple reservoir 303 to system 101, preferably the system is evacuated prior to filling, thus causing the cavitation medium to be drawn into the system (i.e., utilizing ambient air pressure to provide the pressure to fill the system).

After system 100 is filled as described above, the system is sealed and degassed using vacuum pump 119 (step 205). This step typically takes between 30 and 60 minutes, depending primarily upon the capacity of pump 119, the volume of chamber 101, the volume of reservoir 103, the volumes of conduits 105 and 107, and the volume and vapor pressure of the cavitation fluid. In general, the system is pumped down to the limits of the vacuum pump (e.g., less than 1 mm of mercury for liquid metals) or to the vapor pressure of the liquid.

After degassing step 205, a determination is made as to whether additional degassing is required (step 207). In general, the amount of degassing that is required depends on the sensitivity of the reactants to the presence of oxygen and nitrogen (i.e., the greater the sensitivity to oxygen and nitrogen, the greater the need for degassing). If additional degassing is warranted, preferably cavitation is used to tear vacuum cavities within the cavitation medium (step 209). As the newly formed cavities expand, gas from the fluid that remains after the initial degassing step enters into the cavities. During cavity collapse, however, not all of the gas re-enters the fluid. Accordingly a result of the cavitation process is the removal of dissolved gas from the cavitation fluid via rectified diffusion and the generation of bubbles.

Cavitation as a means of degassing the fluid is typically performed within cavitation chamber 101 using cavitation drivers 137. Clearly the invention is not limited to a specific number, type or location of driver. Examples of suitable drivers are given in co-pending U.S. patent application Ser. No. 10/931,918, filed Sep. 1, 2004, entitled Acoustic Driver Assembly for a Spherical Cavitation Chamber; Ser. No. 11/123,388, filed May 5, 2005, entitled Acoustic Driver Assembly With Recessed Head Mass Contact Surface; and 11/068,080, filed Feb. 28, 2005, entitled Hydraulic Actuated Cavitation Chamber, the disclosures of which are incorporated herein in their entirety for any and all purposes. Preferably for high vapor pressure liquids, prior to optional step 209 the use of vacuum pump 119 is temporarily discontinued, for example by closing valve 121 and turning off the pump, thereby minimizing the loss of cavitation medium through boiling. For low vapor pressure liquids such as liquid metals, vacuum pump 119 can be operated continuously. After the fluid within chamber 101 is cavitated for a period of time, typically for at least 5 minutes and preferably for more than 30 minutes, the newly created bubbles float to the top of the chamber due to their buoyancy. The gas removed from the fluid during this step is periodically removed from the reactor system using vacuum pump 119. Typically the vacuum pump is only used after there has been a noticeable increase in pressure within system 100, preferably an increase of at least 0.2 psi over the vapor pressure of the cavitation fluid, alternately an increase of at least 0.02 psi over the vapor pressure of the cavitation fluid, or alternately an increase of a couple of percent of the vapor pressure. Preferably the use of cavitation as a means of degassing the cavitation fluid is continued until the amount of dissolved gas within the cavitation fluid is so low that the fluid will no longer cavitate at the same cavitation driver power.

Figure 4:
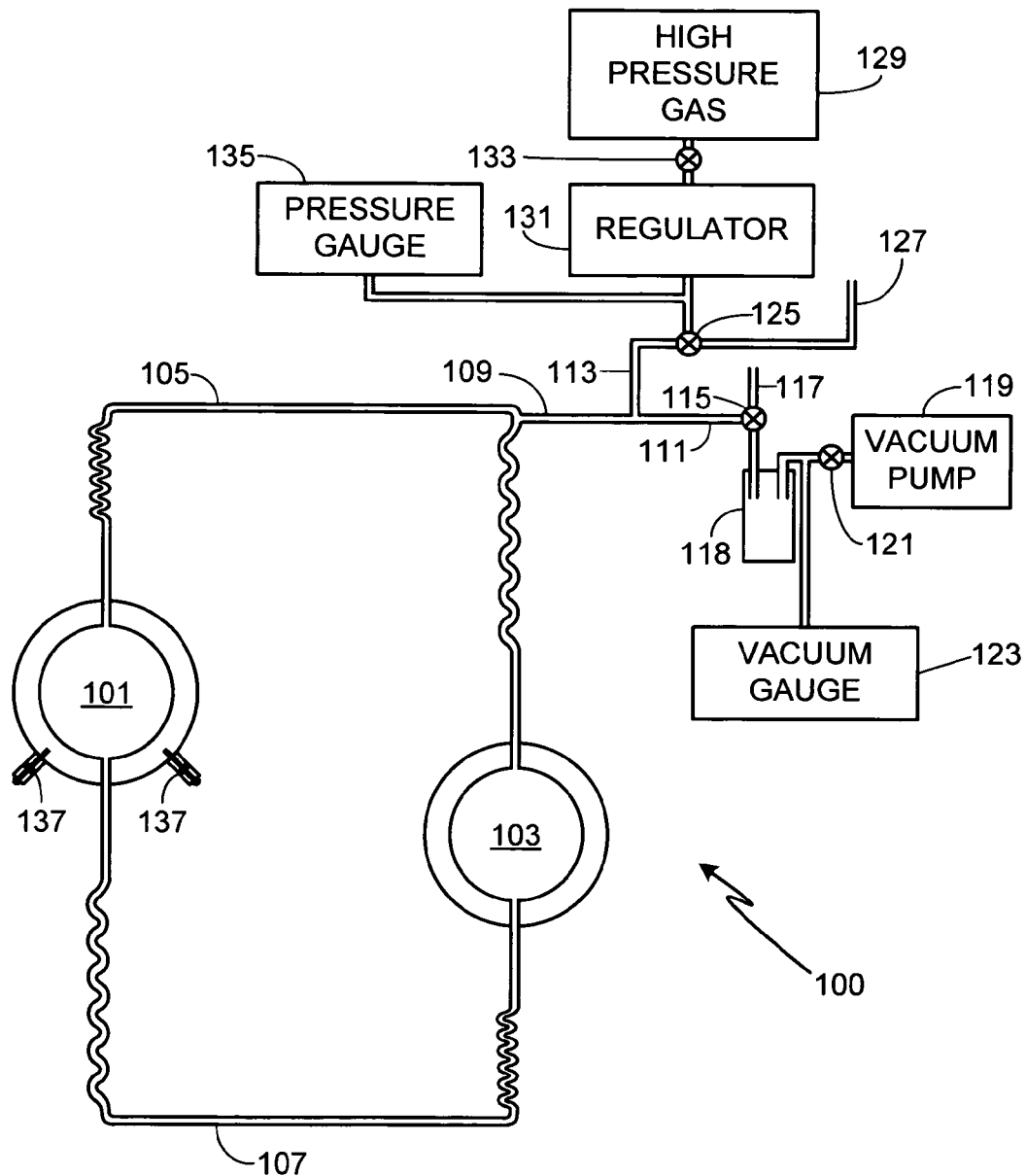
FIG. 4 is an illustration of the system of FIG. 1 in which the cavitation chamber is positioned higher than the reservoir, causing the cavitation fluid to flow out of the chamber and into the reservoir.
Figure 5:
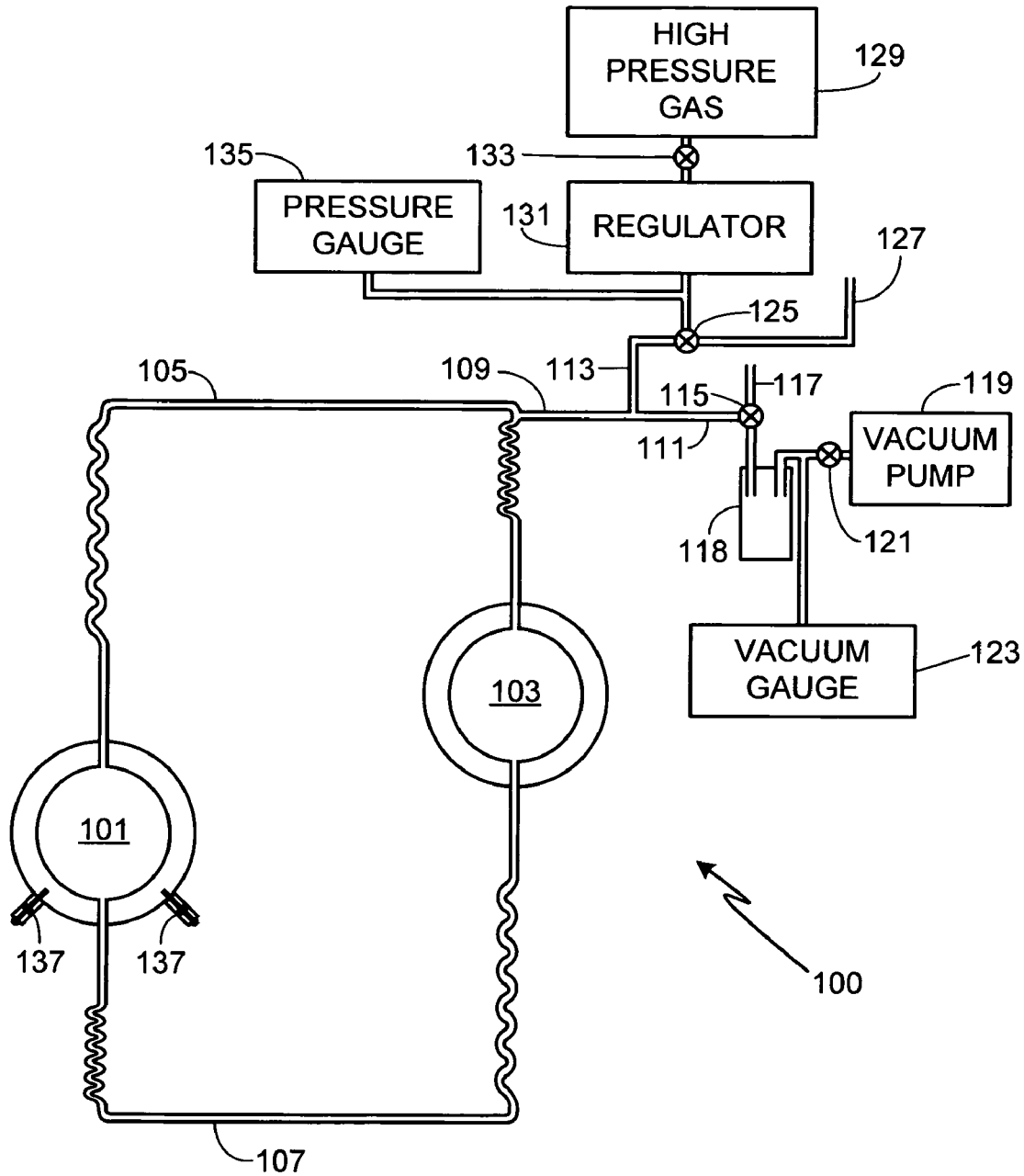
FIG. 5 is an illustration of the system of FIG. 1 in which the cavitation chamber is positioned lower than the reservoir, causing the cavitation fluid to flow out of the reservoir and into the chamber.

After completing the optional cavitation degassing step, preferably the cavitation medium is circulating between chamber 101 and reservoir 103 (step 211), the process being repeated (step 212) until all of the cavitation medium is sufficiently degassed. Fluid circulation is performed by moving the positions of chamber 101 and reservoir 103 relative to one another (see FIGS. 4 and 5), thereby causing the cavitation fluid contained therein to flow back and forth between the two containers. Cavitation aided degassing can either continue throughout the fluid circulation step, or be stopped during step 211 and then reinitiated after the cavitation medium has been sufficiently mixed. FIG. 4 is an illustration of system 100 in which chamber 101 is positioned higher than reservoir 103, causing the cavitation fluid to flow out of chamber 101 and into reservoir 103. FIG. 5 is an illustration of system 100 in which chamber 101 is positioned lower than reservoir 103, causing the cavitation fluid to flow out of reservoir 103 and into chamber 101.

Figure 6:
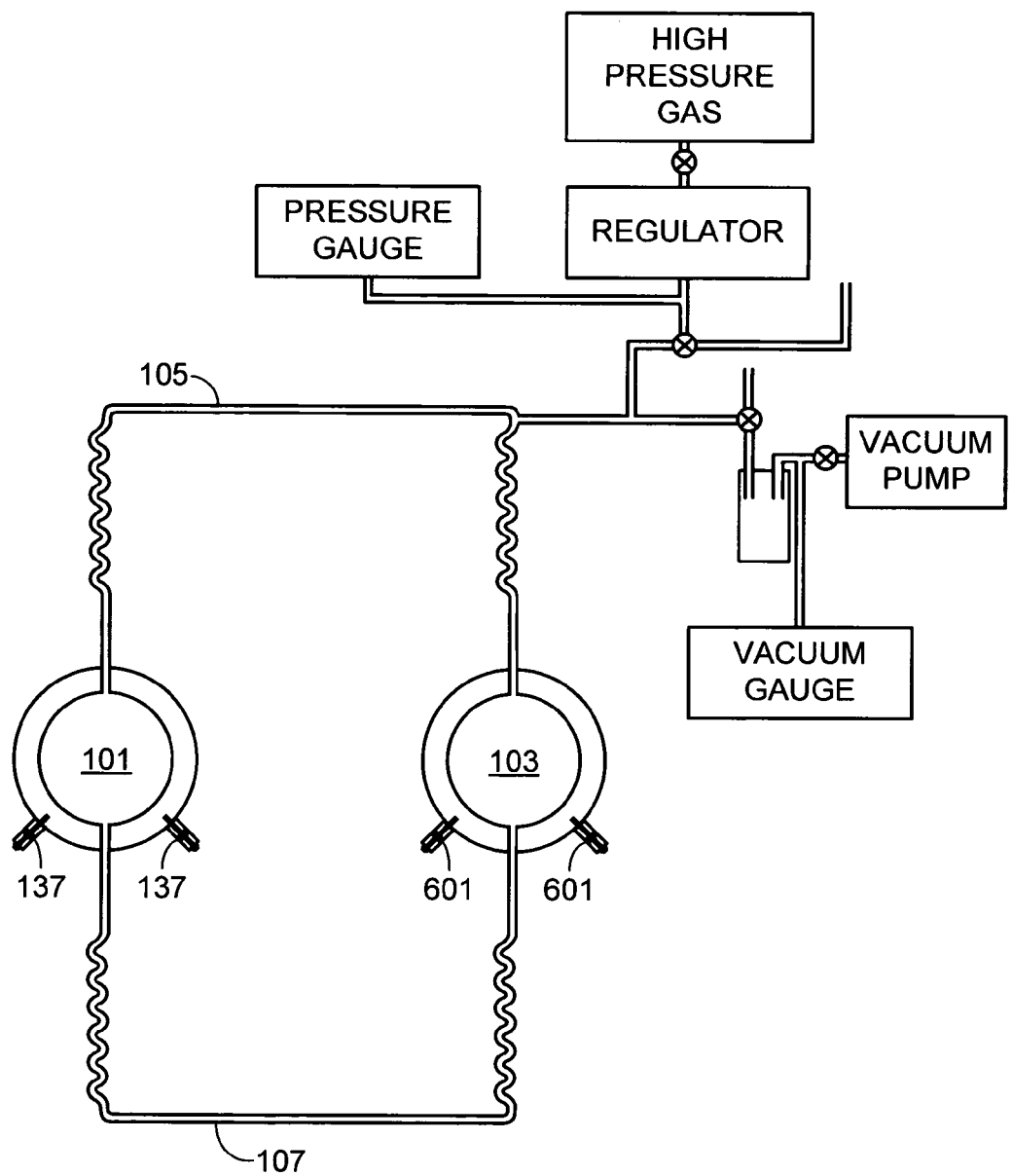
FIG. 6 is an illustration of the system of FIG. 1 in which cavitation drivers are attached to the cavitation fluid reservoir.

As previously noted, preferably cavitation aided degassing step 209 is performed using drivers 137 coupled to chamber 101. Alternately, one or more drivers 601 can be attached to reservoir 103 as illustrated in FIG. 6, drivers 601 allowing step 209 to be performed within reservoir 103. As the attachment of drivers 601 to reservoir 103 does not eliminate the need for drivers 137 which are required for the actual cavitation process, this approach is not preferred. The attachment of one or more cavitation drivers 601 to reservoir 103 does eliminate the need for step 211, assuming that the cavitation aided degassing step is performed within both chamber 101 and reservoir 103.

Once system 100 is sufficiently degassed via step 205 and, if desired, optional steps 209/211, system 100 is sealed off from the vacuum system, for example using valve 115 (step 213), thereby protecting sensitive pressure gauge 123. Then system 100 is pressurized with the desired source (i.e., reactant) gas 129 to the desired pressure in order to load the cavitation medium with the source gas (step 215). In one preferred embodiment, the desired system pressure is between 500 and 1000 psi and source gas 129 is deuterium gas. If desired, source gas 129 can be a mixture of gases.

After completion of step 215 system 100, and more specifically cavitation drivers 137, can be used to cavitate the cavitation medium contained within chamber 101. In a preferred embodiment, however, the concentration of non-source gas in the cavitation medium is further decreased by repeating the degassing and source loading steps. Once again steps 209/211 are optional.

At this point the cavitation system is ready to perform the desired cavitation reactions within chamber 101. Accordingly the cavitation medium within chamber 101 which has been loaded with source gas 129 is cavitated using driver(s) 137, the high intensity cavitation driven implosions within the cavitation medium driving the desired reactions (step 217). During step 217 preferably chamber 101 and reservoir 103 are positioned such that chamber 101 is completely filled, for example as shown in FIG. 5.

As the cavitation driven reactions take place and bubbles are formed and cavitated within the medium, the cavitating medium slowly becomes depleted of source gas 129. To load additional source gas 129 into the medium without re-pressurizing the system, the cavitation fluid is circulated between chamber 101 and reservoir 103 (step 219). Step 219 causes cavitation fluid within reservoir 103 which was previously loaded with source gas 129 but has not yet been depleted to be exchanged with the depleted or partially depleted cavitation medium within chamber 101. To perform step 219 the relative vertical positions of chamber 101 and reservoir 103 are varied as illustrated in FIGS. 4 and 5, thereby causing cavitation fluid to flow between chamber 101 and reservoir 103 via conduit 107. In one embodiment, cavitation within chamber 101 is performed continuously throughout step 219. In an alternate embodiment, cavitation within chamber 101 is suspended during step 219 (i.e., steps 221/223). After the cavitation medium has been sufficiently depleted of source gas 129, either experiments are terminated (step 225) or the cavitation fluid must be reloaded (step 215). If the reaction products are gaseous, then preferably the medium is degassed (step 205) prior to reloading the system.

During cavitation step 217, the inventor has found that slowly bleeding system 100, for example by opening valve 125 to conduit 127 and lowering the pressure at a rate of approximately 10 psi per hour, leads to improved bubble formation (optional step 227).

Figure 7:
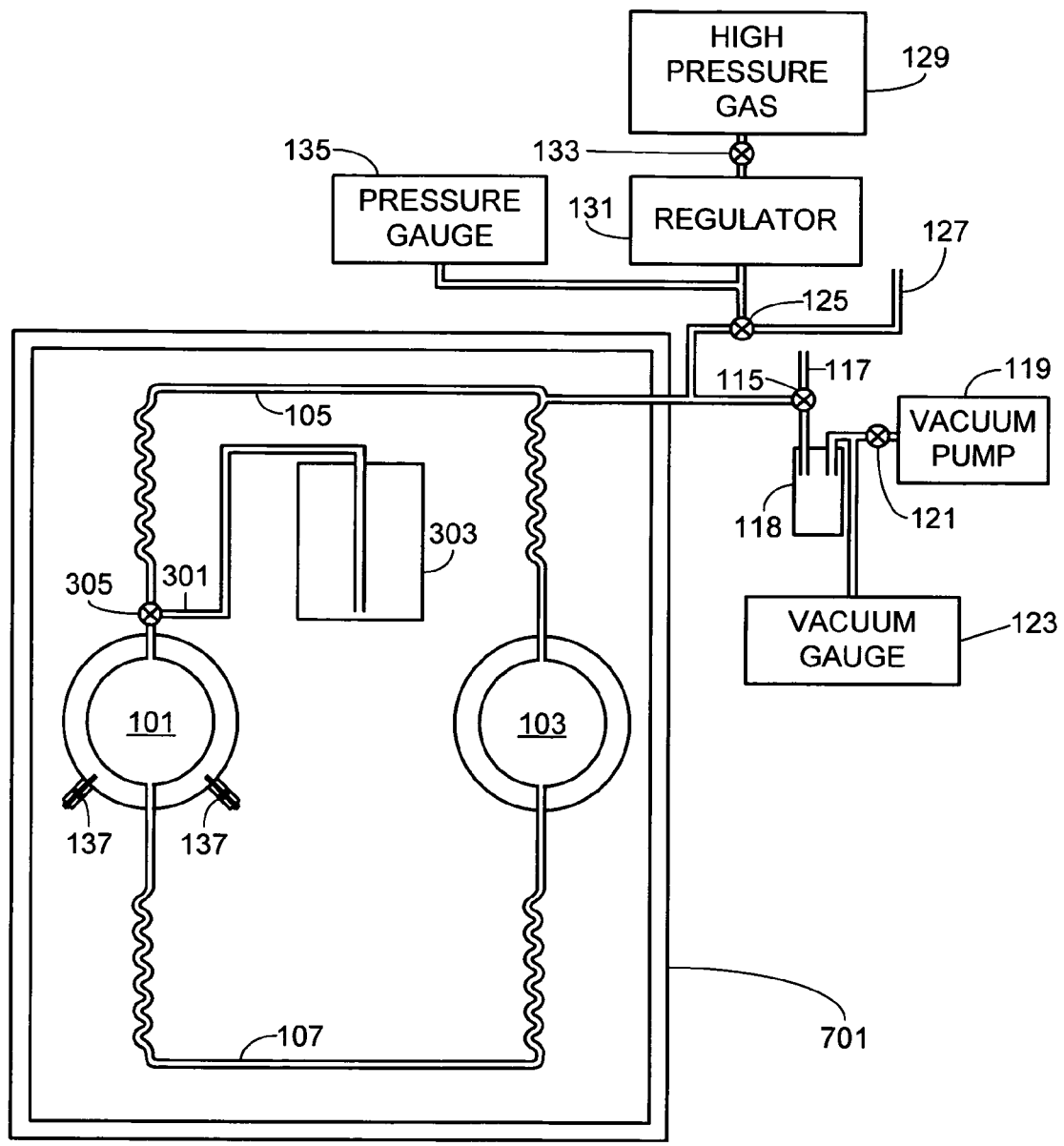
FIG. 7 is an illustration of the system of FIG. 1 with the inclusion of an oven surrounding the cavitation chamber, reservoir and coupling conduits.
Figure 8:
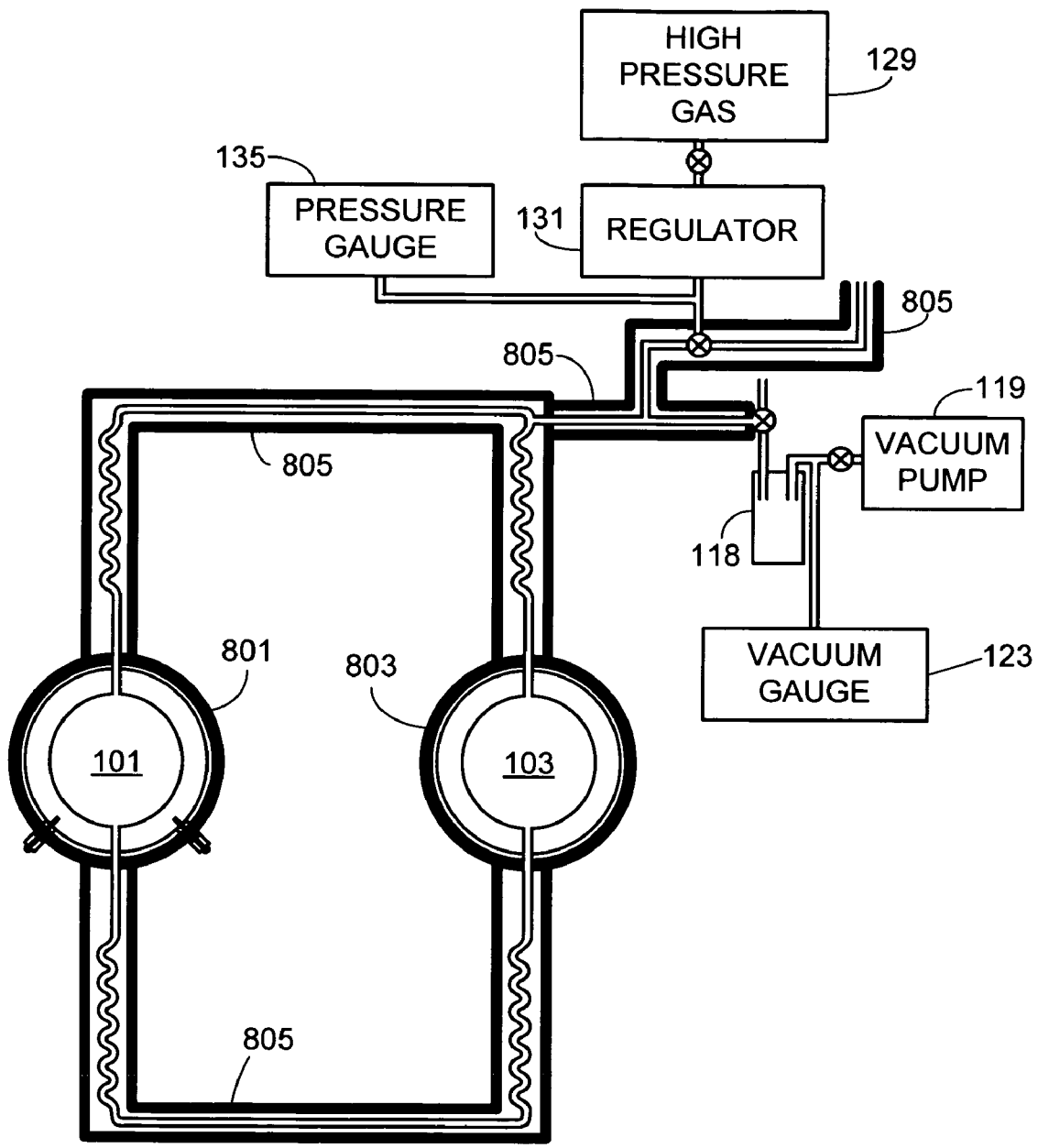
FIG. 8 is an illustration of the system of FIG. 1 with the inclusion of heaters surrounding the cavitation chamber, reservoir and coupling conduits.

As previously noted, the present apparatus and gas loading method can be used with liquid metals, including those metals that have a melting point higher than the ambient temperature. FIG. 7 is an illustration of system 100 modified for use with such cavitation media. Specifically, chamber 101, reservoir 103 and conduits 105/107 are all placed within an oven 701. Conduit 109 passes through the wall of oven 701, thus allowing vacuum pump 119, high pressure gas source 129, regulator 131, and pressure gauges 123/135 to all be maintained at ambient temperature. Although the inventor has found that the system shown in FIG. 7 is the easiest method of consistently maintaining the desired temperature throughout chamber 101, reservoir 103 and conduits 105/107, it is also possible to use localized heaters, for example as illustrated in FIG. 8. It will be appreciated that the use of localized heaters requires that all conduits and/or portions of conduits in which liquid metal may pass be heated. As shown in FIG. 8, chamber 101 is surrounded by a heater 801, reservoir 103 is surrounded by a heater 803, and conduits 105/107 are surrounded/wrapped with a heater 805. If desired, only a portion of conduit 105 can be heated as the cavitation fluid does not fill this conduit, rather the cavitation fluid typically only rises into conduit 105 when the positions of chamber 101 and reservoir 103 are being altered in order to circulate the cavitation medium between them. It will be appreciated that during system operation, drivers 137 will also heat the cavitation medium contained within chamber 101, thereby lowering the heating requirements placed on heater 801.

Regardless of the method of heating (i.e., oven, localized heaters, etc.), in addition to heating chamber 101, reservoir 103 and the portions of conduits 105/107 in which cavitation fluid may flow, it is necessary to heat the initial cavitation fluid holding reservoir 303 as well as any conduits used to couple this reservoir to system 100 during the system filling procedure. Accordingly in the preferred embodiment illustrated in FIG. 7, initial cavitation fluid holding reservoir 303, coupling conduit 301 and valve 305 are all maintained within oven 701. It will be appreciated that coupling conduit 301 can also be attached to other locations within the system (and within oven 701), for example to the upper or lower portions of reservoir 103 or to the bottom portion of chamber 101. In the system illustrated in FIG. 8 it is assumed that reservoir 303 is coupled to conduit 127 during the filling procedure. Accordingly heater 805 also encases conduits 109/113/127 as well as valve 125.

Figure 9:
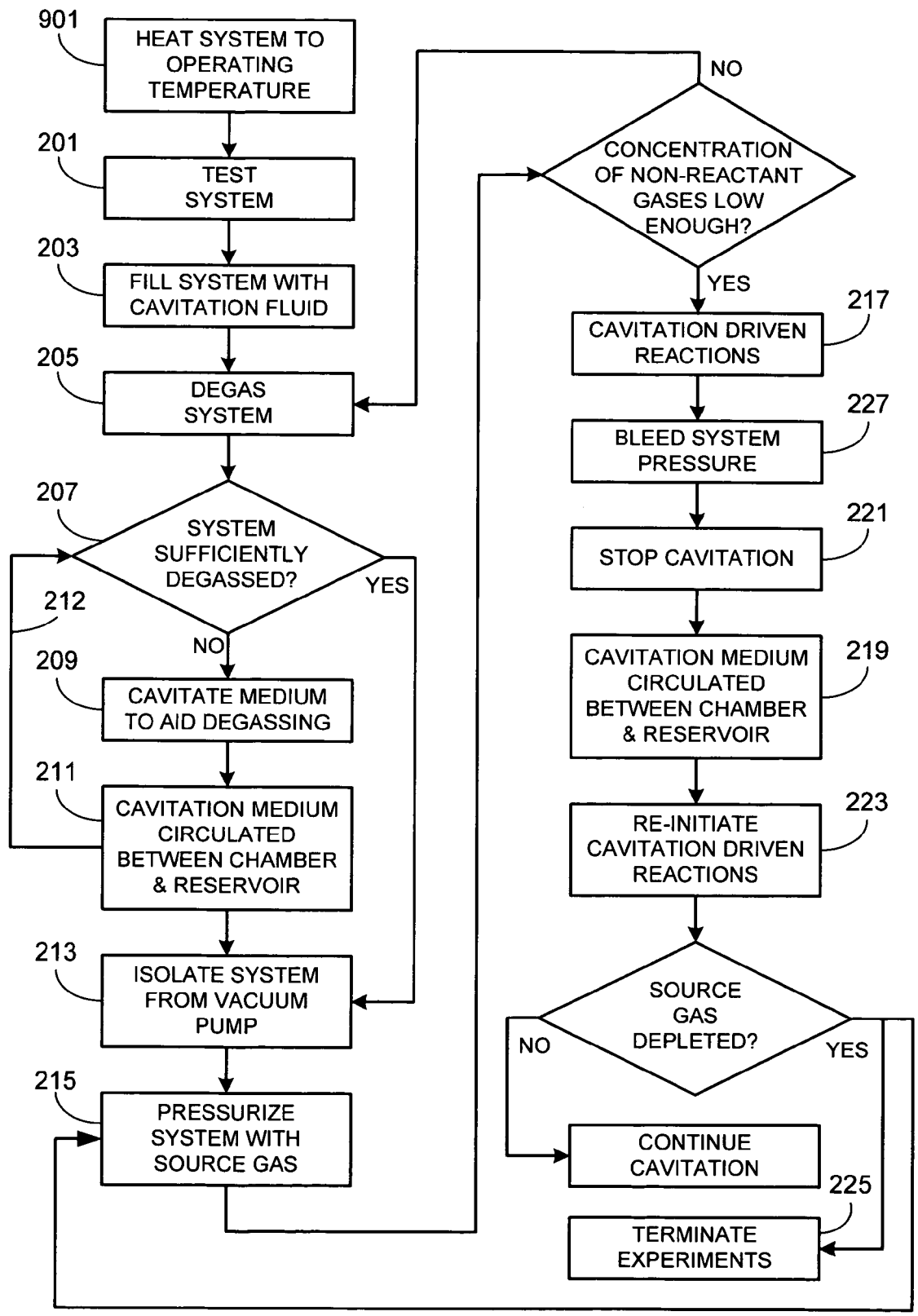
FIG. 9 illustrates the steps performed during use of the gas loading system shown in FIGS. 7 and 8.

The use of the heated system as illustrated in FIGS. 7 and 8 is similar to the approach previously outlined for the non-heated system. However, as illustrated in FIG. 9, an additional system heating step 901 is required. Preferably heating step 901 is performed prior to, or concurrently with, system testing step 201, thus insuring that the system does not have any vacuum or pressure leaks even at the elevated operating temperature.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A configurable cavitation system having at least a first configuration and a second configuration, comprising:
   a cavitation chamber having a first fluid port disposed at or proximal to a lower portion of said cavitation chamber and a second fluid port disposed at or proximal to an upper portion of said cavitation chamber;
   at least one cavitation driver coupled to said cavitation chamber;
   a cavitation medium reservoir having a first fluid port disposed at or proximal to a lower portion of said cavitation medium reservoir and a second fluid port disposed at or proximal to an upper portion of said cavitation medium reservoir;
   a first flexible fluid conduit coupling said first fluid port of said cavitation chamber to said first fluid port of said cavitation medium reservoir;

a second flexible fluid conduit coupling said second fluid port of said cavitation chamber to said second fluid port of said cavitation medium reservoir;

said first flexible fluid conduit adapted and arranged to provide a liquid medium from said first fluid port of said cavitation medium reservoir to said first fluid port of said cavitation chamber in said first configuration of said system; and said second flexible fluid conduit adapted and arranged to provide a liquid medium from said first fluid port of said cavitation chamber to said first fluid port of said cavitation medium reservoir in said second configuration of said system;

wherein said first configuration comprises said cavitation medium reservoir being disposed at a greater relative elevation than said cavitation chamber; and wherein said second configuration comprises said cavitation chamber being disposed at a greater relative elevation than said cavitation medium reservoir.

2. The cavitation system of claim 1, wherein said first and second flexible fluid conduits are comprised of a plastic.

3. The cavitation system of claim 1, wherein said first and second flexible fluid conduits are comprised of a metal.

4. The cavitation system of claim 1, wherein said first and second flexible fluid conduits are comprised of coiled metal tubing.

5. The cavitation system of claim 1, further comprising means for degassing the cavitation medium, said degassing means coupled to said cavitation system.

6. The cavitation system of claim 5, wherein said degassing means further comprises a vacuum pump coupled to said cavitation system.

7. The cavitation system of claim 1, further comprising means for heating said cavitation chamber, said cavitation medium reservoir, said second flexible fluid conduit, and at least a portion of said first flexible fluid conduit to a temperature greater than a melting temperature corresponding to said cavitation medium.

8. The cavitation system of claim 7, wherein said heating means is an oven.

9. A configurable cavitation system having at least a first configuration and a second configuration, comprising:

a cavitation chamber having a fluid port disposed at or proximal to a lower portion of said cavitation chamber;

at least one cavitation driver coupled to said cavitation chamber;

a cavitation medium reservoir having a first fluid port disposed at or proximal to a lower portion of said cavitation medium reservoir and a second fluid port disposed at or proximal to an upper portion of said cavitation medium reservoir;

a flexible fluid conduit coupling said port of said cavitation chamber to said first fluid port of said cavitation medium reservoir;

said flexible fluid conduit adapted and arranged to provide a liquid medium from said fluid port of said cavitation chamber to said first fluid port of said cavitation medium reservoir in said second configuration of said system;

a pressurized gas source coupled to said cavitation system; and at least one valve interposed between said pressurized gas source and said cavitation system, wherein said first configuration comprises said cavitation medium reservoir being disposed at a greater relative elevation than said cavitation chamber; and wherein said second configuration comprises said cavitation chamber being disposed at a greater relative elevation than said cavitation medium reservoir.

10. The cavitation system of claim 9, wherein said flexible fluid conduit is comprised of a plastic.

11. The cavitation system of claim 9, wherein said flexible fluid conduit is comprised of a metal.

12. The cavitation system of claim 9, wherein said flexible fluid conduit is comprised of coiled metal tubing.

13. The cavitation system of claim 9, wherein said pressurized gas source is coupled to said cavitation medium reservoir.

14. The cavitation system of claim 9, further comprising means for degassing the cavitation medium, said degassing means coupled to said cavitation system.

15. The cavitation system of claim 14, wherein said degassing means further comprises a vacuum pump coupled to said cavitation system.

16. The cavitation system of claim 9, further comprising means for heating said cavitation chamber, said cavitation medium reservoir, said flexible fluid conduit, and at least a portion of said flexible fluid conduit to a temperature greater than a melting temperature corresponding to said cavitation medium.

17. The cavitation system of claim 16, wherein said heating means is an oven.

* * * * *